United States Patent
Kramer et al.

(10) Patent No.: US 6,534,507 B1
(45) Date of Patent: Mar. 18, 2003

(54) METHODS FOR TREATING PSYCHOLOGICAL DISORDERS USING BIOACTIVE METABOLITES OF GEPIRONE

(75) Inventors: Stephen J. Kramer, Houston, TX (US); Louis F. Fabre, Houston, TX (US); Edward H. Ruediger, Greefield Park (CA); Joseph P. Yevich, Southington, CT (US)

(73) Assignee: Fabre-Kramer Pharmaceuticals, Inc., Houston, TX (US)

( * ) Notice: Subject to any disclaimer, the term of this patent is extended or adjusted under 35 U.S.C. 154(b) by 0 days.

(21) Appl. No.: 09/709,741

(22) Filed: Nov. 13, 2000

Related U.S. Application Data (60) Provisional application No. 60/172,684, filed on Dec. 20, 1999.

(51) Int. Cl.$^7$ .............................................. A61K 31/506
(52) U.S. Cl. .............................. 514/252.14; 514/252.18
(58) Field of Search ........................ 514/252.14, 252.18, 514/100

(56) References Cited

U.S. PATENT DOCUMENTS

| | | |
|---|---|---|
| 4,423,049 A | 12/1983 | Temple, Jr. |
| 4,956,368 A | 9/1990 | Cipollina et al. |
| 5,478,572 A | 12/1995 | David et al. |

OTHER PUBLICATIONS

L. L. von Moltke et al., *Gepirone and 1–(2–pyrimidinyl)–piperazine in vitro: Human Cytochromes Mediating Transformation and Cytochrome Inhibitory Effects, Psychopharmacology*, (1998), 140: 293–299; XP–001037530.

Joseph A. Cipollina et al., *Synthesis and Biological Activity of the Putative Metabolites of the Atypical Antipsychotic Agent Tiospirone, J. Med. Chem.*, 1991, vol. 34, No. 11, 3316–3328; XP–002157852.

Edward H. Kerns et al., *Monitoring in vitro Experiments Using Microdialysis Sampling O–Line Wth Mass Spectrometry, Journal of Pharmaceutical and Biomedical Analysis*, vol. 20 (1999), pp. 115–128; XP–000972965.

S.M. Stahl, "Essential Psychopharmacology, Neuroscientific Basis and Clinical Applications", Cambridge University Press, 1996, Chapters 5 and 7, pp. 97–130 and 167–215(1998).

*Primary Examiner*—Frederick Krass
(74) *Attorney, Agent, or Firm*—Oblon, Spivak, McClelland, Maier & Neustadt, P.C.

(57) ABSTRACT

Bioactive gepirone metabolites, such as 3-OH gepirone (4,4,-dimethyl-3-hydroxy-1-[4-[4-(2-pyrimidinyl)-1-piperazinyl]butyl]-2,6-piperidinedione), and their pharmaceutically acceptable salts and hydrates, can be used to alleviate psychological disorders or the symptoms thereof. The use of these compounds provides advantages over other therapeutic azapirones as they possess superior bioavailability, faster onset of action, and more stable plasma levels when administered to a mammal.

40 Claims, 6 Drawing Sheets

3-OH-Gepirone Plasma Levels

| Time (H) | 01 MGM | 01 MGM | 02 R-P | 02 R-P | 03 EMP | 03 EMP | 04 MLK | 04 MLK |
|---|---|---|---|---|---|---|---|---|
| 0.00 | B.L.Q. | 3.27 | B.L.Q. | 4.06 | B.L.Q. | 2.89 | B.L.Q. | 2.01 |
| 0.50 | B.L.Q. | 3.55 | B.L.Q. | 3.78 | B.L.Q. | 3.49 | B.L.Q. | 1.95 |
| 0.75 | B.L.Q. | 3.34 | B.L.Q. | 4.32 | 0.511 | 4.61 | B.L.Q. | 2.49 |
| 1.00 | 0.743 | 3.68 | B.L.Q. | 4.22 | 1.14 | 4.86 | 0.554 | 3.89 |
| 1.50 | 2.01 | 4.25 | B.L.Q. | 5.88 | 2.86 | 5.71 | 1.57 | 2.90 |
| 2.00 | 3.01 | 5.08 | B.L.Q. | 5.67 | 3.49 | 6.62 | 2.95 | 3.38 |
| 2.50 | 3.45 | 4.85 | B.L.Q. | 6.36 | 3.92 | 6.04 | 2.69 | 4.17 |
| 3.00 | 4.74 | 4.54 | 1.19 | 6.13 | 3.69 | 5.42 | 3.86 | 4.19 |
| 3.50 | 4.77 | 5.49 | 3.26 | 7.04 | 3.51 | 5.43 | 3.51 | 4.91 |
| 4.00 | 5.06 | 5.02 | 2.68 | 5.98 | 3.16 | 6.00 | 3.42 | 3.66 |
| 5.00 | 5.18 | 5.39 | 5.06 | 6.41 | 4.00 | 5.21 | 3.69 | 5.26 |
| 6.00 | 5.27 | 4.60 | 4.91 | 6.58 | 4.03 | 6.54 | 3.81 | 5.32 |
| 8.00 | 4.76 | 5.71 | 5.25 | 5.91 | 4.30 | 6.10 | 3.82 | 6.33 |
| 12.00 | 4.14 | 4.31 | 3.65 | 5.04 | 4.20 | 5.01 | 3.58 | 4.11 |
| 16.00 | 3.80 | 4.53 | 4.23 | 4.99 | 3.03 | 4.18 | 2.92 | 4.11 |
| 24.00 | 4.00 | 3.27 | 2.13 | 3.97 | 2.16 | 2.36 | 1.62 | 4.01 |
| 30.00 | 1.64 | 2.75 | 2.20 | 2.56 | 0.884 | 1.31 | 1.26 | 2.15 |
| 36.00 | 0.874 | 1.47 | 1.52 | 1.76 | 0.559 | 0.904 | 0.743 | 1.18 |
| 48.00 | 0.290 | 0.570 | 0.812 | 0.702 | B.L.Q. | 0.273 | B.L.Q. | 0.327 |
| 94.00 | 1.29 | *** | 2.19 | *** | 3.78 | *** | 0.369 | *** |
| 106.00 | 3.54 | *** | 3.89 | *** | 2.83 | *** | 1.80 | *** |

\*\*\* = No Sample

FIG. 2B

3-OH-Gepirone Plasma Levels

| 05 JAB | 05 JAB | 06 MLR | 06 MLR | 07 GWS | 07 GWS | 08 GTL | 08 GTL | 09 MLJ | 09 MLJ | 10 E-M | 10 E-M | 11 GCK | 11 GCK |
|---|---|---|---|---|---|---|---|---|---|---|---|---|---|
| B.L.Q. | 4.77 | B.L.Q. | 3.41 | B.L.Q. | 1.89 | B.L.Q. | 6.98 | B.L.Q. | 8.31 | B.L.Q. | 2.35 | B.L.Q. | 14.41 |
| B.L.Q. | 6.49 | B.L.Q. | 3.50 | 0.897 | 2.35 | B.L.Q. | 6.77 | 2.32 | 11.25 | B.L.Q. | 3.11 | 0.333 | 9.10 |
| 0.892 | 5.90 | 0.819 | 3.93 | 1.78 | 2.78 | 0.557 | 7.96 | 3.73 | 10.22 | 0.309 | 6.51 | 0.850 | 9.93 |
| 1.45 | 5.72 | 1.42 | 5.14 | 1.50 | 3.68 | 1.19 | 8.70 | 4.93 | 11.06 | 1.30 | 6.33 | 1.27 | 14.12 |
| 2.05 | 6.46 | 1.95 | 5.25 | 3.25 | 4.10 | 1.48 | 8.82 | 6.16 | 13.67 | 5.37 | 9.18 | 5.50 | 12.70 |
| 3.98 | 8.31 | 2.55 | 5.31 | 3.15 | 3.99 | 3.91 | 9.60 | 6.00 | 14.25 | 5.09 | 11.13 | 6.71 | 14.82 |
| 5.13 | 7.05 | 2.86 | 5.47 | 3.31 | 6.07 | 4.70 | 11.00 | 6.47 | 14.89 | 6.19 | 10.89 | 4.91 | 12.71 |
| 4.20 | 7.08 | 3.26 | 6.57 | 6.86 | 6.16 | 5.43 | 9.66 | 8.12 | 12.62 | 7.29 | 10.22 | 9.74 | 13.19 |
| 5.34 | 8.13 | 3.78 | 5.92 | 5.41 | 5.48 | 5.34 | 8.11 | 7.55 | 14.63 | 11.06 | 8.34 | 6.70 | 15.91 |
| 4.73 | 9.28 | 3.24 | 8.57 | 5.28 | 7.64 | 8.40 | 9.60 | 8.18 | 15.03 | 7.21 | 11.12 | 5.29 | 15.65 |
| 5.05 | 8.23 | 4.45 | 5.67 | 6.92 | 8.55 | 6.62 | 10.32 | 6.69 | 13.16 | 8.23 | 11.56 | 6.75 | 15.39 |
| 4.10 | 7.54 | 4.78 | 6.26 | 8.70 | 7.17 | 9.18 | 11.07 | 6.81 | 14.21 | 7.81 | 11.40 | 8.09 | 11.65 |
| 4.72 | 7.59 | 4.50 | 5.51 | 7.32 | 5.50 | 8.57 | 11.21 | 7.57 | 10.64 | 8.62 | 11.74 | 6.98 | 14.38 |
| 5.39 | 5.49 | 4.12 | 5.44 | 3.61 | 5.92 | 6.06 | 8.12 | 8.62 | 10.04 | 7.28 | 8.33 | 5.88 | 7.46 |
| 4.73 | 6.32 | 4.97 | 5.84 | 1.66 | 3.90 | 5.50 | 8.34 | 7.66 | 8.60 | 8.71 | 9.78 | 7.57 | 13.13 |
| 3.26 | 4.15 | 3.68 | 3.83 | 0.662 | 2.29 | 4.09 | 7.74 | 4.53 | 7.34 | 3.73 | 9.65 | 5.21 | 6.48 |
| 1.62 | 2.84 | 2.36 | 3.68 | 1.36 | 1.36 | 4.13 | 5.20 | 2.37 | 5.39 | 4.24 | 7.52 | 6.10 | 4.95 |
| 0.903 | 2.38 | 1.80 | 2.31 | B.L.Q. | 0.776 | 2.90 | 5.44 | 1.22 | 4.16 | 2.82 | 5.32 | 4.90 | 3.38 |
| 0.438 | 1.49 | 0.469 | 0.867 | B.L.Q. | 0.251 | 1.54 | 1.72 | 0.279 | 2.02 | 0.809 | 1.59 | 1.50 | 1.73 |
| 5.52 | *** | *** | *** | 0.570 | *** | *** | *** | 6.17 | *** | 8.93 | *** | 10.76 | *** |
| 4.65 | | 0.283 | | 0.819 | | 1.68 | | 2.80 | | 3.90 | | 8.43 | |

*** = No Sample

FIG. 2C

3-OH-Gepirone Plasma Levels

| 12DWL | 12DWL | 13 JIR | 13 JIR | 14 KEC | 14 KEC | 15 BLC | 15 BLC | 16 DJS | 16 DJS | 17 DCJ | 17 DCJ | 18 ARA | 18 ARA |
|---|---|---|---|---|---|---|---|---|---|---|---|---|---|
| B.L.Q. | 3.94 | B.L.Q. | 5.98 | B.L.Q. | 4.93 | B.L.Q. | 3.71 | B.L.Q. | 1.01 | B.L.Q. | 4.12 | B.L.Q. | 3.95 |
| B.L.Q. | 5.66 | B.L.Q. | 4.98 | 6.47 | 5.43 | 0.721 | 3.35 | B.L.Q. | 1.46 | 1.55 | 9.15 | B.L.Q. | 4.02 |
| 0.764 | 6.43 | 0.609 | 5.52 | 0.626 | 6.46 | 1.36 | 4.99 | 0.782 | 3.00 | 2.26 | 8.16 | 0.982 | 4.12 |
| 0.846 | 7.41 | 1.11 | 5.83 | 1.03 | 5.96 | 2.07 | 5.13 | 1.39 | 2.90 | 2.95 | 7.57 | 1.92 | 5.29 |
| 4.84 | 8.56 | 1.45 | 8.24 | 2.15 | 5.74 | 2.81 | 4.56 | 2.49 | 3.62 | 4.86 | 6.66 | 3.95 | 5.63 |
| 5.68 | 9.60 | 1.73 | 7.46 | 2.94 | 5.71 | 4.00 | 4.69 | 3.24 | 4.57 | 5.53 | 8.32 | 3.97 | 7.54 |
| 4.69 | 10.88 | 2.17 | 7.29 | 3.97 | 6.82 | 4.20 | 6.15 | 3.70 | 5.07 | 4.17 | 9.75 | 4.89 | 10.30 |
| 5.27 | 10.64 | 2.09 | 7.15 | 4.52 | 5.68 | 4.73 | 6.52 | 4.18 | 7.06 | 6.11 | 7.24 | 4.88 | 9.41 |
| 6.17 | 8.95 | 2.84 | 8.40 | 4.59 | 7.24 | 5.28 | 6.01 | 4.45 | 10.87 | 7.43 | 7.59 | 3.98 | 6.71 |
| 5.87 | 9.73 | 3.74 | 7.52 | 5.32 | 8.70 | 4.92 | 7.27 | 5.10 | 7.04 | 5.92 | 7.56 | 6.38 | 10.43 |
| 5.76 | 9.86 | 3.41 | 7.57 | 5.83 | 7.44 | 5.17 | 7.14 | 6.30 | 7.69 | 7.05 | 8.73 | 6.70 | 10.21 |
| 6.61 | 9.65 | 3.20 | 7.25 | 6.79 | 7.57 | 5.24 | 7.80 | 7.25 | 9.18 | 4.75 | 7.59 | 7.42 | 8.66 |
| 6.87 | 7.74 | 3.32 | 6.89 | 6.50 | 7.57 | 4.90 | 2.36 | 4.26 | 6.82 | 5.95 | 5.91 | 4.87 | 6.21 |
| 5.03 | 6.84 | 4.43 | 5.79 | 5.79 | 6.14 | 5.01 | 2.56 | 4.41 | 4.05 | 4.42 | 6.99 | 5.27 | 7.28 |
| 5.35 | 6.00 | 2.17 | 5.09 | 3.83 | 5.62 | 3.72 | 1.80 | 3.53 | 6.26 | 3.37 | 6.46 | 4.22 | 5.71 |
| 3.74 | 4.62 | 2.40 | 4.70 | 3.22 | 4.95 | 1.95 | 1.20 | 2.89 | 3.48 | 1.20 | 4.90 | 3.00 | 2.93 |
| 2.07 | 2.90 | 1.92 | 3.33 | 3.00 | 4.25 | 0.827 | 1.42 | 1.95 | 1.53 | 0.537 | 3.20 | 2.90 | 1.58 |
| 1.96 | 2.97 | 0.952 | 2.11 | 1.62 | 2.16 | 0.545 | 0.965 | 0.985 | 1.01 | 0.399 | 1.84 | 1.74 | 1.30 |
| 0.926 | 1.20 | 0.408 | 0.822 | 0.824 | 1.25 | 0.268 | 0.576 | 0.361 | 0.646 | B.L.Q. | 0.746 | 0.786 | 0.580 |
| 2.87 | *** | 1.36 | *** | 3.62 | *** | 2.57 | *** | 1.89 | *** | 1.34 | *** | 2.26 | *** |
| 5.17 | | 3.92 | | 3.62 | | 3.32 | | 6.17 | | 4.80 | | 4.21 | |

*** = No Sample

FIG. 2D

3-OH-Gepirone Plasma Levels

| 19 GDG | 19 GDG | 20 DNS | 20 DNS | 21 MLQ | 21 MLQ | 22 RRT | 22 RRT | 23 ESB | 23 ESB | 24 ABC | 24 ABC | 25 STN | 25 STN |
|---|---|---|---|---|---|---|---|---|---|---|---|---|---|
| B.L.Q. | 1.41 | B.L.Q. | 4.72 | B.L.Q. | 2.73 | B.L.Q. | 6.50 | B.L.Q. | 3.81 | B.L.Q. | 1.37 | B.L.Q. | 2.65 |
| B.L.Q. | 1.53 | 2.22 | 5.67 | 0.310 | 4.06 | B.L.Q. | 6.55 | 1.15 | 9.93 | 1.39 | 2.19 | 0.398 | 5.34 |
| 1.35 | 2.23 | 2.33 | 8.64 | 1.14 | 4.79 | 0.399 | 7.36 | 2.94 | 5.19 | 1.55 | 2.31 | 2.82 | 6.88 |
| 1.52 | 3.05 | 3.47 | 9.36 | 2.79 | 5.05 | 0.895 | 8.26 | 2.70 | 7.42 | 2.80 | 2.97 | 3.80 | 6.78 |
| 3.84 | 4.68 | 3.98 | 7.06 | 3.31 | 5.58 | 4.14 | 8.41 | 4.51 | 10.31 | 3.27 | 4.19 | 5.91 | 8.13 |
| 4.76 | 7.01 | 4.12 | 8.20 | 5.36 | 6.50 | 2.99 | 9.40 | 3.97 | 9.55 | 3.76 | 3.63 | 5.49 | 7.58 |
| 4.42 | 3.90 | 3.56 | 7.53 | 6.62 | 5.72 | 3.20 | 8.43 | 3.53 | 7.42 | 4.23 | 4.95 | 6.42 | 5.86 |
| 5.80 | 6.44 | 4.81 | 7.75 | 6.80 | 7.63 | 3.79 | 6.60 | 3.95 | 6.89 | 4.05 | 5.15 | 7.29 | 7.62 |
| 6.44 | 4.98 | 8.13 | 6.46 | 6.82 | 8.19 | 3.44 | 7.83 | 3.91 | 7.51 | 4.91 | 4.21 | 6.55 | 7.10 |
| 5.88 | 5.32 | 0.873 | 7.52 | 7.42 | 7.91 | 4.72 | 7.51 | 4.15 | 8.52 | 4.55 | 5.39 | 5.95 | 7.35 |
| 6.18 | 6.26 | 2.43 | 8.19 | 8.78 | 7.67 | 3.71 | 7.69 | 4.36 | 8.88 | 4.75 | 4.99 | 6.98 | 7.26 |
| 7.06 | 7.18 | 3.13 | 6.84 | 8.93 | 8.42 | 3.63 | 8.17 | 3.57 | 8.33 | 5.08 | 6.05 | 7.96 | 6.61 |
| 5.25 | 7.85 | 5.26 | 6.82 | 6.77 | 6.75 | 4.60 | 6.27 | 3.98 | 7.18 | 4.92 | 4.84 | 7.18 | 8.14 |
| 4.21 | 6.41 | 4.29 | 5.42 | 5.55 | 6.78 | 2.70 | 9.45 | 3.69 | 7.44 | 3.63 | 4.35 | 5.94 | 4.74 |
| 4.51 | 6.80 | 2.81 | 5.90 | 3.61 | 5.83 | 2.26 | 5.61 | 5.14 | 7.00 | 2.65 | 2.94 | 5.34 | 6.71 |
| 3.51 | 4.61 | 3.97 | 5.46 | 2.14 | 3.22 | 1.79 | 3.16 | 4.20 | 5.01 | 0.909 | 1.28 | 2.25 | 4.10 |
| 3.88 | 3.55 | 4.55 | 2.60 | 1.25 | 1.96 | 3.15 | 3.66 | 2.55 | 4.09 | 0.459 | 0.889 | 1.21 | 1.92 |
| 2.53 | 3.41 | 5.07 | 2.55 | 1.04 | 1.41 | 1.04 | 2.36 | 1.40 | 4.73 | B.L.Q. | 0.410 | 0.722 | 1.31 |
| 1.17 | 1.64 | 4.50 | 0.899 | 0.404 | 0.657 | 0.742 | 1.19 | 0.329 | 1.66 | 0.276 | B.L.Q. | 0.550 | 0.499 |
| 5.27 | *** | 4.11 | *** | 4.08 | *** | 3.61 | *** | 1.97 | *** | 1.74 | *** | 6.01 | *** |
| 5.86 | *** | 3.94 | *** | 2.54 | *** | 2.50 | *** | 3.37 | *** | 3.13 | *** | 1.76 | *** |

*** = No Sample

FIG. 2E

3-OH-Gepirone Plasma Levels

| 26 XVD | 26 XVD | 27 MQW | 27 MQW | 28 NB | 28 NB | 29 MJC | 29 MJC |
|---|---|---|---|---|---|---|---|
| B.L.Q. | 1.55 | B.L.Q. | 3.32 | B.L.Q. | 1.61 | B.L.Q. | 4.54 |
| B.L.Q. | 1.80 | 0.860 | 5.38 | 1.65 | 3.33 | 2.24 | 7.48 |
| 0.822 | 3.40 | 1.84 | 5.39 | 3.77 | 4.05 | 2.25 | 7.36 |
| 1.29 | 5.34 | 2.58 | 5.59 | 2.77 | 7.08 | 2.30 | 14.46 |
| 3.14 | 4.88 | 3.76 | 6.82 | 4.02 | 7.12 | 3.76 | 14.82 |
| 2.87 | 6.73 | 4.46 | 6.03 | 3.76 | 6.26 | 4.41 | 9.34 |
| 5.25 | 5.61 | 4.57 | 6.50 | 6.12 | 7.74 | 6.40 | 13.75 |
| 9.90 | 5.56 | 5.00 | 7.46 | 5.94 | 12.17 | 6.71 | 10.46 |
| 7.09 | 6.50 | 4.95 | 7.91 | 8.76 | 7.35 | 9.15 | 14.61 |
| 5.55 | 7.89 | 5.79 | 8.21 | 7.22 | 8.60 | 9.74 | 10.13 |
| 8.24 | 7.61 | 6.30 | 7.64 | 10.38 | 14.64 | 10.02 | 14.82 |
| 8.60 | 6.86 | 5.37 | 7.59 | 7.92 | 8.82 | 11.21 | 10.25 |
| 8.71 | 7.43 | 5.45 | 6.32 | 6.71 | 6.08 | 8.21 | 8.76 |
| 4.19 | 4.68 | 4.29 | 3.92 | 5.25 | 3.27 | 6.45 | 7.08 |
| 3.99 | 3.18 | 3.27 | 3.59 | 4.17 | 2.57 | 5.12 | 5.40 |
| 3.16 | 1.56 | 2.76 | 4.04 | 2.11 | 1.14 | 1.64 | 1.90 |
| 1.57 | 0.841 | 1.35 | 2.17 | 0.787 | 0.586 | 1.18 | 1.14 |
| 1.04 | 0.538 | 0.897 | 1.62 | 0.843 | 0.345 | 0.550 | 0.752 |
| 0.831 | 0.271 | 0.667 | 0.708 | 0.298 | B.L.Q. | B.L.Q. | 0.443 |
| 0.889 | *** | 4.22 | *** | B.L.Q. | *** | 0.976 | *** |
| 0.798 |  | 3.78 |  | 5.63 |  | 3.48 |  |

*** = No Sample

METHODS FOR TREATING PSYCHOLOGICAL DISORDERS USING BIOACTIVE METABOLITES OF GEPIRONE

This application claims priority to U.S. provisional application No. 60/172,684, filed Dec. 20, 1999.

FIELD OF THE INVENTION

The invention involves the alleviation of depression, anxiety, and other psychological or mental disorders by administering certain bioactive metabolites of the known anti-depressant compound gepirone. In a preferred embodiment, the compound is 4,4,-dimethyl-3-hydroxy-1-[4-[4-(2-pyrimidinyl)-1-piperazinyl]butyl]-2,6-piperidinedione (3-OH gepirone), however other gepirone metabolites and combinations thereof are possible and contemplated. Surprisingly, these bioactive metabolites of gepirone show improved bioavailability characteristics and improved potential for immediate action and long-term treatment regimens when compared to gepirone and other therapeutic azapirones. Accordingly, the invention provides new and improved methods for treating a variety of psychological disorders and conditions.

DISCUSSION OF RELATED TECHNOLOGY

The use, preparation, and characterization of therapeutic azapirone compounds has been disclosed in numerous documents (see Cadieux, *Amer. Family Physician* 1996 53: 2349–2353; Temple, U.S. Pat. No. 4,423,049; Gawin, U.S. Pat. No. 5,185,329; Madding, U.S. Pat. No. 5,521,313). This class of compounds attributes its activity to partial agonism of the 5-HT$_{1A}$ receptor.

Clinical studies of known 5-HT$_{1A}$ agonists and partial agonists, for example buspirone, ipsapirone, and gepirone, have shown that these compounds are useful in the treatment of anxiety disorders, such as generalized anxiety disorder (GAD), panic disorder, and obsessive compulsive disorder (Glitz, D. A., Pohl, R., *Drugs* 1991, 41:11; Cadieux, *Amer. Family Physician* 1996 53: 2349–2353). Clinical and preclinical evidence supports 5-HT$_{1A}$ partial agonists for use in treating depression as well as impulse control disorders and alcohol abuse (van Hest, *Psychopharm.*, 107: 474 (1992); Schipper et al, *Human Psychopharm.*, 6: S53 (1991); Cervo et al, *Eur. J. Pharm.*, 158: 53 (1988); Glitz, D. A., Pohl, R., *Drugs*, 41: 11(199 1)). Studies show that 5-HT$_{1A}$ agonists and partial agonists inhibit isolation-induced aggression in male mammals, indicating that they can be used to treat aggression (Sanchez et al, *Psychopharmacology*, 1993, 110:53–59). Other studies indicate that 5-HT$_{1A}$ receptors are important in the serotonergic modulation of haloperidol-induced catalepsy (Hicks, *Life Science* 1990, 47:1609) suggesting that 5-HT$_{1A}$ agonists can be used to treat the deleterious side effects of conventional antipsychotic agents, such as haloperidol. Recent reports show that this is the case for side effects like tardive dyskinesias.

One of the more important azapirones is gepirone, which has the following structure.

gepirone

Gepirone has been used to effectively treat anxiety disorders and depression (Casacalenda, *Canadian J. of Psychiatry*, 43:722–730 (1998)). However, it has several drawbacks from the standpoint of an ideal therapeutic anxiolytic or anti-depressant. It has low bioavailability characteristics when delivered orally, on the order of 14–18%. In addition, the half-life of gepirone is very short. As a result, an extended release formulation of gepirone is preferred so that sustained therapeutic levels can be delivered during a standard regimen without increasing dosage levels. Furthermore, in a small percentage of cases, gepirone has been associated with side effects such as nausea and vomiting. Accordingly, 5-HT$_{1A}$ agonists with improved properties and characteristics are still in need.

Several proposed gepirone-derived compounds were discussed in von Malke, et al., *Psychopharmacology*, 140: 293–299 (1998). No biological activity for these compounds has been disclosed or suggested. The metabolism of buspirone, perhaps the best known member of the azapirones, was elucidated by Jajoo, et al, *Xenobiotica*, 20:779–786 (1990). In the metabolic cascade derived from buspirone, one of the seven buspirone metabolites (referred to as 6'-OH-Bu) is the buspirone analog of 3-OH gepirone. No significant biological activity has been disclosed for 6'-OH-Bu.

SUMMARY AND DETAILED DESCRIPTION OF THE INVENTION

Certain bioactive metabolites of gepirone, especially 4,4,-dimethyl-3-hydroxy-1-[4-[4-(2-pyrimidinyl)-1-piperazinyl]butyl]-2,6-piperidinedione (3-OH gepirone) have been found to be agents useful in treating anxiety, depression, and a number of other psychological disorders. 3-OH gepirone has the following structural formula.

3-OH gepirone

Examples of other bioactive gepirone metabolites are listed below.

5-OH gepirone

The bioactive gepirone metabolites of this invention include those compounds listed above that can be used to treat psychological disorders, or that functionally interact with a 5-HT$_{1A}$ receptor. A bioactive gepirone metabolite includes any active salt form, hydrate form, enantiomeric form 3,5-dihydroxy gepirone or mixture, or crystal form of the compound. Preferably, the bioactive gepirone metabolite is 3-OH gepirone.

As improved 5-HT$_{1A}$ agonists, 3-OH gepirone and the other bioactive gepirone metabolites can be used in methods to alleviate a number of psychological disorders. Preferred methods alleviate depression, anxiety, generalized anxiety disorder, panic disorder, obsessive compulsive disorder, alcohol abuse, addiction, atypical depression, infantile autism, major depressive disorder, depression with melancholia, premenstrual syndrome, and attention deficit hyperactivity disorder or symptoms of these disorders. The method comprises administering an effective amount of the bioactive gepirone metabolite, or a pharmaceutically acceptable salt or hydrate thereof, to a mammal. Preferably, the bioactive gepirone metabolite of these methods is selected from the group consisting of 3-OH gepirone, 3,5-dihydroxy gepirone, and 5-OH gepirone. The method may employ any one of these compounds. However, combinations of these metabolites, or combinations of the metabolites with other active or inert ingredients, are also contemplated.

The invention concerns methods for ameliorating depression, anxiety, or psychological disorders in a mammal in need of such treatment, which comprises administering to the mammal an effective amount or dose of a bioactive gepirone metabolite such as 3-OH gepirone. As used herein, the administration of a bioactive gepirone metabolite includes the administration of any active salt form, hydrate form, enantiomeric form or mixture, or crystal form of the compound. An effective oral dose should, in general, be in the range of from about 0.1 to 2 mg per kg of body weight. Alternatively, the effective dose or delivery system should result in plasma concentrations in the range of about 1 ng/ml to about 20 ng/ml, preferably about 1 ng/ml to about 5 ng/ml. The compounds like 3-OH gepirone can be administered via oral, sublingual, buccal, transdermal, rectal, or transnasal routes, thereby minimizing destructive first-pass metabolism. Systemic administration of 3-OH gepirone may be by a parenteral route, e.g. intramuscular, intravenous, subcutaneous, etc. Systemic administration may also be achieved by oral administration of a prodrug, a precursor or derivative form of 3-OH gepirone or gepirone metabolite. In this case the precursor or derivative form minimizes destructive metabolism of 3-OH gepirone or functions physiologically to release it into the mammal's system. One skilled in the art is familiar with methods to achieve this. In accordance with good clinical practice, it is preferable to administer 3-OH gepirone, or a precursor form, at concentration levels that will produce effective antidepressant and/or anxiolytic effects without causing harmful or untoward side-effects.

The invention also concerns compositions comprising 3-OH gepirone, or 5-OH gepirone, or 3,5-dihydroxy gepirone, or a combination of any of them. Preferably, these compositions are prepared to be administered to a mammal. Administration to a mammal can be by any number of drug deliver routes (See, for example, *Remington's Pharmaceutical Sciences*, 18th Edition, Genero et al. eds., Easton: Mack Publishing Co. for a description of a variety of drug delivery technologies available to one skilled in the art for use here). Preferably, the delivery route is an oral formulation, a parenteral formulation, or a transdermal formulation.

Formulations comprising 3-OH gepirone, 5-OH gepirone, or 3,5-dihydroxy gepirone, or the bioactive metabolite of gepirone, can be given in a oral dosage forms or parenteral forms comprised of an effective antidepressant and/or anxiolytic amount of 3-OH gepirone, 5-OH gepirone, or 3,5-dihydroxy gepirone, or one of the pharmaceutically acceptable acid addition salts thereof, or a hydrate thereof, in a pharmaceutically acceptable carrier. A variety of carriers are known in the art. Pharmaceutical compositions that provide from about 5 to 50 mg of the active ingredient per unit dose are preferred and are conventionally prepared as tablets, pills, capsules, aqueous solutions, and aqueous or oily suspensions. 3-OH gepirone, 5-OH gepirone, and 3,5-dihydroxy gepirone can also be given orally when compounded in a precursor or prodrug form in an oral dosing formulation such as a tablet, lozenge, capsule, syrup, elixir, aqueous solution or suspension.

From metabolism studies conducted in the rat, the following metabolic scheme has emerged.

Scheme 1: Proposed Metabolic Scheme of Gepirone in Rats

From extensive in vitro binding studies, 3-OH gepirone has been found to be highly selective for the 5-HT$_{1A}$ receptor among the serotonergic receptor subtypes. 3-OH gepirone appears to have only weak binding affinity for dopaminergic and alpha-adrenergic receptors. In this regard, 3-OH gepirone is even more selective than gepirone.

The following discussion addresses comparative receptor binding results for 3-OH gepirone, gepirone, and two other reference agents. The two reference agents are buspirone and 1-pyrimidinylpiperazine (1-PP), a metabolite common to both buspirone and gepirone.

As known in the art, human monoamine GPCR binding profiles were obtained using heterologously expressed cloned human GPCRs in the binding experiments. Both pKi and IC$_{50}$ (nM concentration) values were obtained as well as an average value of each from at least three determinations. 3-OH gepirone shows high selectivity (at least about 30 fold lower to over 1500 fold lower IC$_{50}$ values) for the 5-HT$_{1A}$ receptor compared to the 5-HT$_2$, 5-HT$_6$, and 5-HT$_7$ receptors. The IC$_{50}$ for each of gepirone, 3-OH gepirone, and buspirone are below 100 nM for 5-HT$_{1A}$ (approximately 58 nM for 3-OH gepirone). However, for each of gepirone and buspirone the IC$_{50}$ values for the 5-HT$_7$ receptor is much lower than for 3-OH gepirone, from 3–12×lower, and the IC$_{50}$ values for the 5-HT$_{2A}$ receptor is lower as well (from 70% lower to over 3.5×lower). This indicates that gepirone and buspirone interact with the 5-HT$_7$ and 5-HT$_{2A}$ receptors much more specifically and at lower concentrations than does 3-OH gepirone. The IC$_{50}$ values for the 5-HT$_6$ receptor were high for all the compounds tested. In summary, 3-OH gepirone demonstrates a better selectivity profile than the other agents tested. As a result, 3-OH gepirone possesses an improved side effect profile compared to gepirone and buspirone since the potential for interacting with receptors other than 5-HT$_{1A}$ is markedly lower.

Dopaminergic receptors D2A, D2B, D3, and D4 were also tested. With the exception of the relatively weak binding at D4 (approximately 1421 nM $IC_{50}$), 3-OH gepirone shows insignificant dopaminergic binding. Similarly, 3-OH gepirone and the other compounds did not display significant affinity at alpha-adrenergic receptors with the exception of weak binding at the Alpha 2C receptor (Alpha 2A, Alpha 2B, and Alpha 2C tested).

In the muscarinic receptor binding data, gepirone, 3-OH gepirone, and 1-PP do not exhibit any affinity for muscarinic receptors ($M_1$, $M_2$, $M_3$, or $M_4$), with pKi values below 4.34 for all four receptor subtypes. Treatment with 3-OH gepirone likely results in a superior side effect profile than the comparative buspirone and gepirone.

In sum, the bioactive gepirone metabolites exemplified by 3-OH gepirone exhibit a selective binding profile indicative of compounds that can be used clinically for treatment of anxiety, depression, and other psychological disorders.

Figure 2A:
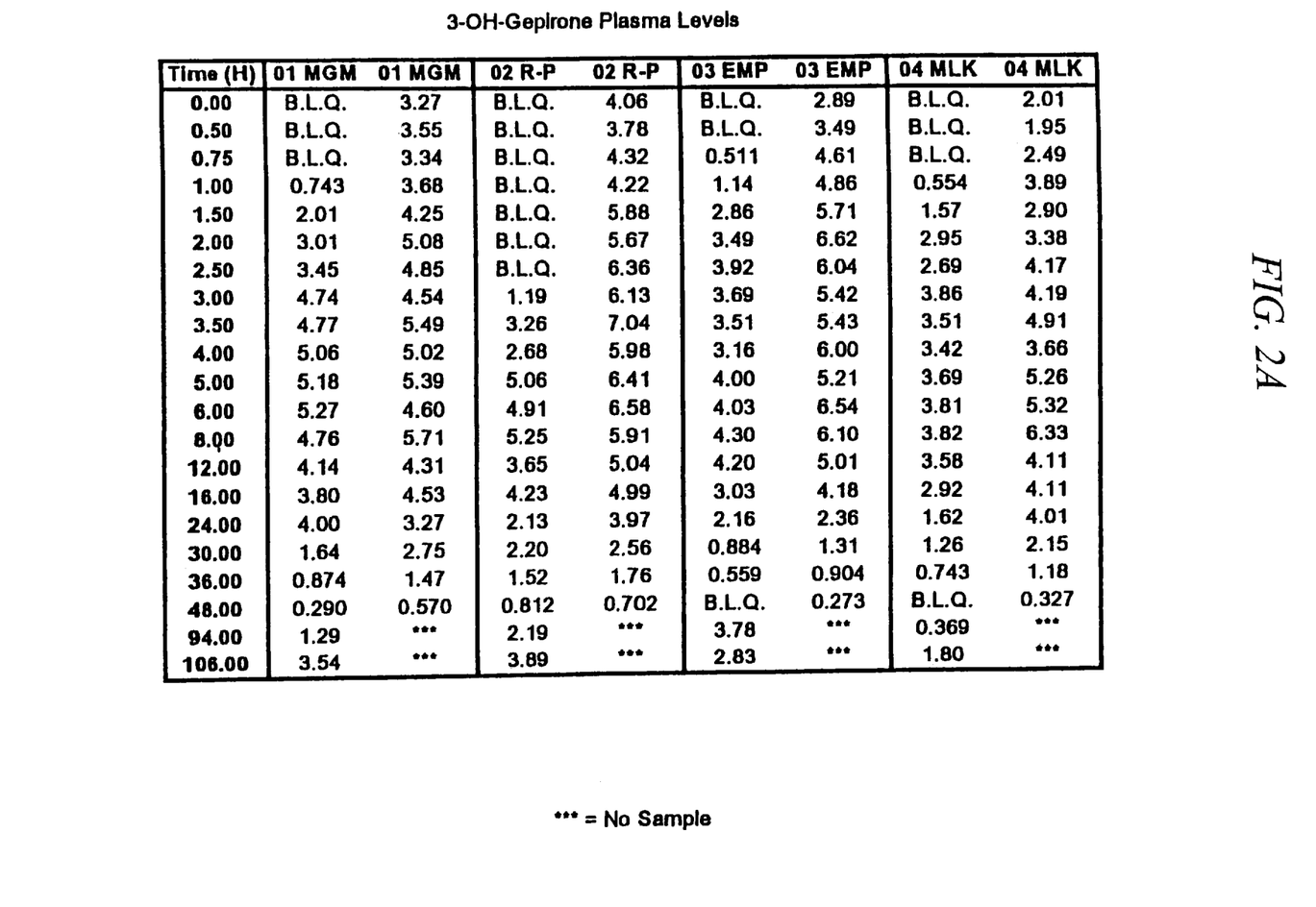
FIG. 2 is a table showing the time course of plasma levels of 3-OH-gepirone present in plasma (ng/ml) after administration of gepirone to human subjects. "Time (H)" represents time after administration.
Figure 2B:
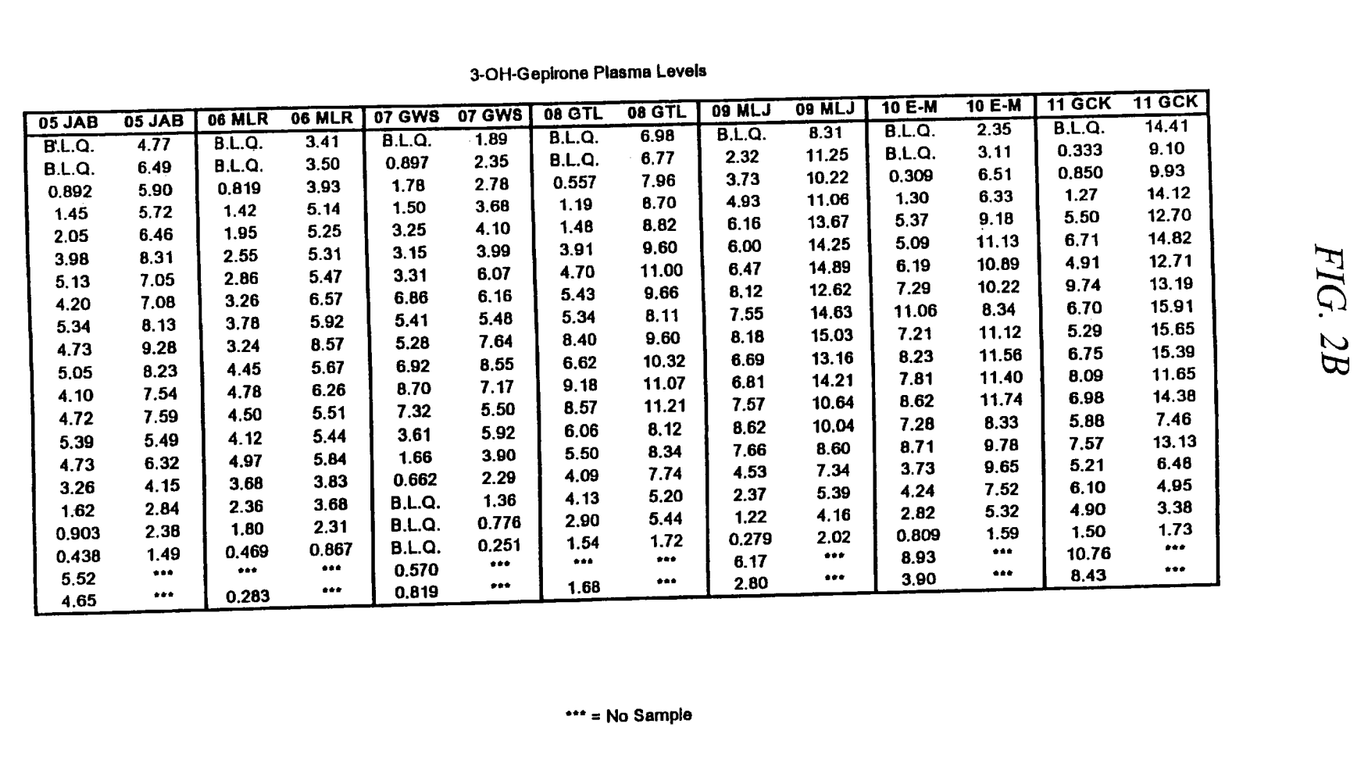
Figure 2E:
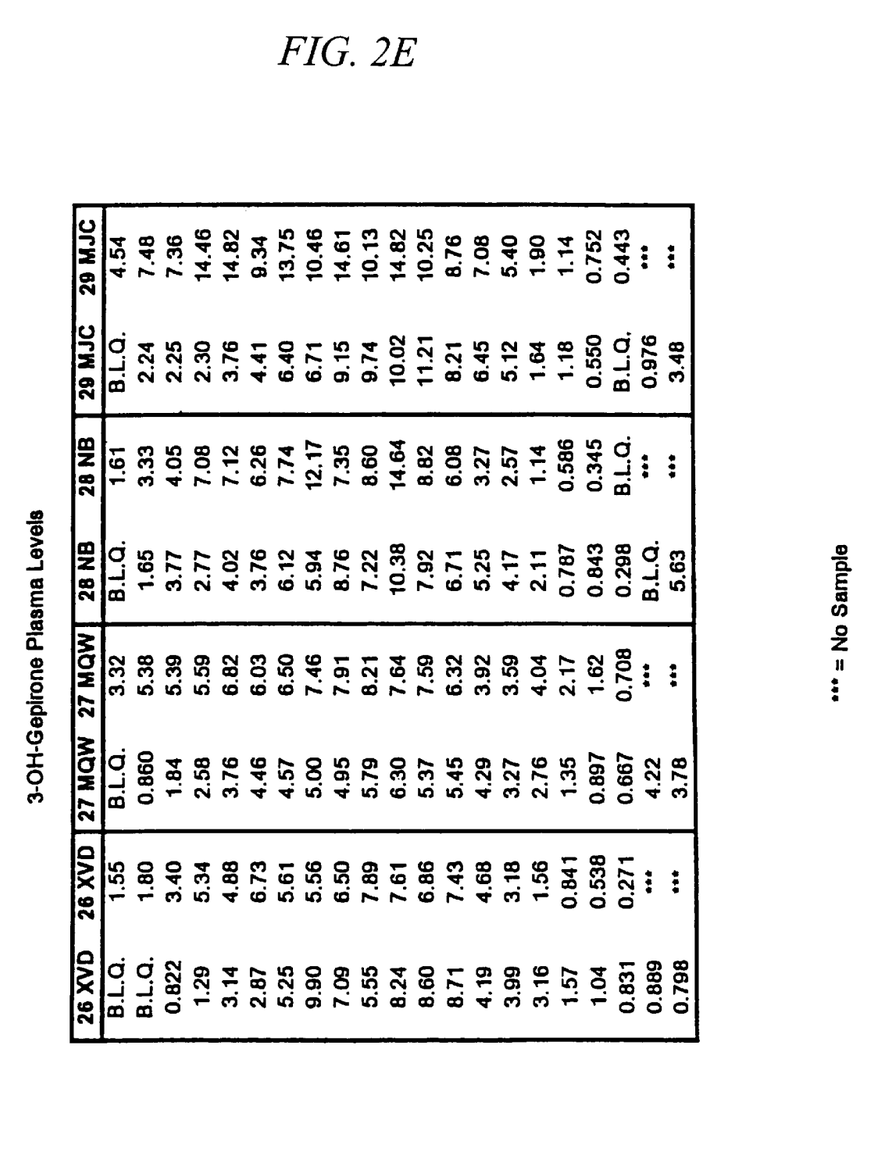

In addition, data shows that 3-OH gepirone will act as a much superior immediate action therapeutic compared to gepirone and buspirone. FIG. 2 depicts the plasma levels of 3-OH gepirone in a number of human subjects who were administered a dose of gepirone. Clearly, 3-OH gepirone is available quickly and persists in the plasma for extended periods of time. In contrast, both gepirone and buspirone have very short half-lives and low bioavailibilty profiles (about 1% for buspirone and 14–18% for gepirone). Without being limited by this theory, the inventors consider the additional-OH group on 3-OH gepirone compound and the other bioactive gepirone metabolites as affording an improved water solubility characteristic compared to gepirone and buspirone. This improved characteristic reduces the first-pass degradation of 3-OH gepirone in liver (see also Example 2 below).

Accordingly, the 3-OH gepirone compound and the similar bioactive gepirone metabolites possess superior properties compared to gepirone and buspirone when the compound is used in a pharmaceutical composition or for treating psychological disorders.

The pharmaceutically acceptable acid addition salts of 3-OH gepirone and the bioactive gepirone metabolites are also considered useful as antidepressant or anxiolytic agents or in treating psychological disorders. By definition, these are salts in which the anion does not contribute significantly to toxicity or pharmacological activity of the base form of 3-OH gepirone or the bioactive gepirone metabolite.

Acid addition salts are obtained by methods known in the art and can encompass a reaction of 3-OH gepirone or the bioactive gepirone metabolite with an organic or inorganic acid, preferably by contact in solution. Examples of useful organic acids are carboxylic acids such as maleic acid, acetic acid, tartaric acid, propionic acid, fumaric acid, isethionic acid, succinic acid, pamoic acid, and the like; useful inorganic acids are hydrohalide acids such as HCl, HBr, HI; sulfuric acid; phosphoric acid; and the like. An HCl acid salt of 3-OH gepirone is preferred.

As non-limiting examples, acid salts of the bioactive gepirone metabolites may also include: acetate, adipate, alginate, aspartate, benzoate, benzenesulfonate, bisulfate, butyrate, citrate, camphorate, camphorsulfonate, cyclopentanepropionate, digluconate, dodecylsulfate, methanesulfonate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts may also be employed and non-limiting examples of base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products can also be obtained.

Preferred oral compositions are in the form of tablets or capsules and in addition to 3-OH gepirone or a precursor form of 3-OH gepirone may contain conventional excipients such as binding agents (e.g., syrup, acacia, gelatin, sorbitol, tragecanth, or polyvinyl pyrrolidone), fillers (e.g., lactose, sugar, maize-starch, calcium phosphate, sorbitol or glycine), lubricants (e.g., magnesium stearate, talc, polyethyleneglycol or silica), disintegrants (e.g., starch), and wetting agents (e.g., sodium lauryl sulfate). Solutions or suspensions of 3-OH gepirone with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active ingredient (3-OH gepirone or a pharmaceutically acceptable acid addition salt or hydrate thereof) in water or a vehicle consisting of a polyhydric aliphatic alcohol such as glycerine, propylene glycol, and polyethylene glycols or mixtures thereof. The polyethylene glycols consist of a mixture of non-volatile, normally liquid, polyethylene glycols, which are soluble in both water and organic liquids and which have molecular weights from about 200 to 1500.

3-OH gepirone and the bioactive gepirone metabolites may also be prepared in a transdermal delivery method or other extended release delivery method (see U.S. Pat. Nos. 5,837,280, 5,633,009, and 5,817,331, each specifically incorporated herein by reference). One skilled in the art is familiar with numerous methods for designing and optimizing formulations and delivery methods to deliver the 3-OH gepirone and bioactive gepirone metabolites in effective and non-toxic ways. Remington's Pharmaceuticals Sciences, 18th Edition (specifically incorporated herein by reference), can be relied on and used for these purposes, especially Part 8 therein, "Pharmaceutical Preparations and Their Manufacture."

3-OH gepirone may be synthesized by methods readily available in the chemical literature and known to one skilled in synthetic organic chemistry. One method of preparation utilizes gepirone as a starting material and the process is shown in Scheme 2.

Scheme 2: Preparation of 3-OH Gepirone

This method of preparation is provided as a helpful example and illustrates a convenient synthesis of 3-OH gepirone. A method in van Molke, et al., *Psychopharmacology*, 140: 293–299 (1998), specifically incorporated herein by reference, can be used to produce 3-OH gepirone and the other bioactive metabolites of gepirone by enzymatic (human or rat liver microsomes) conversion of gepirone in vitro. Isolation or purification of the 3-OH gepirone compounds can be by the method described in FIG. 1 or other methods known in the art (see Odontiadis, *J. Pharmaceut. Biomedical Analysis* 1996 14:347–351, specifically incorporated herein by reference).

Systemic administration may be accomplished by administration of a precursor or prodrug form of 3-OH gepirone (e.g., gepirone) to mammals, resulting in systemic introduction of 3-OH gepirone.

Description of Exemplary and Specific Embodiments

The uses of the compounds that constitute this invention and the methods of preparation will appear more fully in light of the following examples, which are given for the purpose of illustration only and are not to be construed as limiting the invention in sphere or scope. All of the references referred to in this specification, for whatever purpose, can be used and relied on to make and used specific embodiments of the invention. Thus, all of the references are specifically incorporated into this disclosure by reference.

EXAMPLE 1

Preparation of 3-OH Gepirone (I)

A. Di-4-nitrobenzyl peroxydicarbonate (III) Di-4-nitrobenzyl peroxydicarbonate was prepared using a modification of the literature procedure (Strain, et al., *J Am. Chem. Soc.*, 1950, 72:1254; specifically incorporated herein by reference). Thus, to an ice-cold solution of 4-nitrobenzyl chloroformate (10.11 g, 4.7 mmol) in acetone (20 mL) was added dropwise over 30 min an ice-cold mixture of 30% $H_2O_2$ (2.7 mL, 24 mmol) and 2.35 N NaOH (20 mL, 47 mmol). The mixture was vigorously stirred for 15 min and then it was filtered and the filter-cake was washed with water and then with hexane. The resulting damp solid was taken up in dichloromethane, the solution was dried ($Na_2SO_4$) and then it was diluted with an equal volume of hexane. Concentration of this solution at 20° C. on a rotary evaporator gave a crystalline precipitate which was filtered, washed with hexane and dried in vacuo to give compound III (6.82 g, 74%) as pale yellow microcrystals, mp 104° C. (dec).

Di-4-nitrobenzyl peroxydicarbonate was found to be a relatively stable material, which decomposed as its melting point with slow gas evolution. In comparison, dibenzyl peroxydicarbonate (Cf Gore and Vederas, *J. Org. Chem.*, 1986, 51:3700; specifically incorporated herein by reference) decomposed with a sudden vigorous expulsion of material from the melting point capillary.

B. 4.4-Dimethyl-3-(4-nitrobenzyloxycarbonyloxy)-1-[4-[4-(2-pyrimidinyl)-1piperazinyl]butyl]-2.6-piperidinedione (II)

To a solution of 4-dimethyl-1-[4-[4-(2-pyrimidinyl)-1-piperazinyl]butyl]-2,6-piperidinedione (gepirone: 12.7 g, 356 mmole) in dry THF (200 mL) was added LiN (Me₃Si)₂ (37.3 mL of a 1 M THF solution) at −78° C. and the mixture was stirred for 2.5 h. A solution of di-4-nitrobenzyl peroxydicarbonate (15 g) in dry THF (100 mL) was then added dropwise over 1 h. Stirring was continued at −78° C. for an additional 2 h.

The cooling bath was then removed and the reaction solution was poured into a mixture of H₂O and EtOAc. The organic phase was separated and washed with H₂O and then with brine. The organic phase was dried and then evaporated to a brown gum. Flash chromatography of the gum, eluting the silica gel column with EtOAc, gave crude product which was titrated in hexane to provide 7.5 g (58%) product (II) with recovery of 2.5 g of gepirone after elution of the column with acetone.

C. 4.4-Dimethyl-3-hydroxy-1-[4-[4-(2-pyrimidinyl)-1-piperazinyl]butyl]-2.6-piperidinedione (I: 3-OH gepirone)

A mixture of II (7.0 g; 12.6 mmole) and 10% Pd/C (3.5 g) in MeOH (70 mL) was hydrogenated in a Parr shaker at 30 psi for 0.5 h. The hydrogenation mixture was filtered through a Celite pad, which was then washed with THF. The filtrate was evaporated to a gum which was solidified by tritration in ether. Filtration gave 2 g of crude product as a beige solid. The filtrate was evaporated and the residue was flash chromatographed through a silica column eluting with EtOAc to provide an additional 1 g of crude product. The crude product was combined and suspended in MeOH. A small portion of ether was added and the mixture was filtered to give 2.5 g of I (3-OH gepirone) as a white solid. This material was recrystallized (acetone-hexane) to give a solid mp 122–124° C. (gas evolution).

Anal. Calcd. for $C_{19}H_{29}N_5O_3 \cdot 0.2\ H_2O$: C, 60.20; H, 7.81; N, 18.47.

Found: C, 60.21; H, 7.79; N, 18.32.

EXAMPLE 2

Comparison of 3-OH Gepirone and Gepirone Metabolites to Ggeplirone

As a basis for estimating the bioavailability of potential therapeutic compounds, a number of octanol-water partition coefficient calculations have been used (see Poole, *J. of Chromatography B*, 745:117–126 (2000); Ishizaki, *J. Pharm. Pharmacol.*, 49:762–767 (1997) (each specifically incorporated herein by reference)). Using these partition coefficients, the bioavailability of gepirone metabolites can be calculated.

| | log $P_{OW}$ Partition Coefficient Octanol-Water | | |
|---|---|---|---|
| Compound | Crippen fragmentation | Viswanadhan's fragmentation | Broto's fragmentation |
| gepirone | 1.38 ± 0.47 | 1.32 ± 0.49 | 1.13 ± 0.97 |
| 3-OH gepirone | 0.73 ± 0.47 | 0.89 ± 0.49 | −0.23 ± 1.11 |

In all methods, 3-OH gepirone possesses higher water solubility (lower log $P_{ow}$) and lower lipid-solubility as compared to gepirone.

The short half-life characteristics of gepirone can be attributed to its high lipid solubility, which makes it much more susceptible to first-pass degradation by the liver. Since 3-OH gepirone is less soluble in lipid, its first pass degradation characteristics will result in a much longer half-life in plasma. Furthermore, the range in lipid solubility for 3-OH gepirone (about 5:1 to 8:1), when the Broto calculation is discarded because of the high standard deviation, is within that generally accepted as appropriate for psychoactive compounds that may interact within receptors in the brain. Accordingly, 3-OH gepirone possesses superior characteristics from the standpoint of an immediate acting pharmaceutical compound that avoids the first-pass degradation by the liver.

EXAMPLE 3

Dosage of 3-OH Gepirone

The 3-OH gepirone compositions and dosage forms of the invention are designed to deliver an effective anxiolytic, anti-depressant, or psychoactive amount of 3-OH gepirone or a pharmaceutically acceptable salt thereof to a mammal, preferably a human. Effective doses of about 0.01 to 40 mg/kg body weight are contemplated, preferred ranges are about 0.1 to about 2 mg per kg body weight. For certain central nervous system disorders, 15 to 90 mg/day, preferably 30–60 mg/day, are recommended. See U.S. Pat. No. 4,771,053 to Cott et al. (specifically incorporated herein by reference). Administration of bioactive gepirone metabolites according to the present invention may be made by the parenteral, oral, buccal, rectal, or transdermnal routes. The oral route is preferred, however. The clinical dosage range for alleviation of major depressive disorders is expected to be less than about 100 mg per day, generally in the 15 to 90 mg range, and preferably in the range of 30–60 mg per day. Since the dosage should be tailored to the individual patient, the usual practice is to commence with a dose of about 5 mg administered once, twice, or three times per day and then to increase the dose every 2 or 3 days by 5 mg at each dosage time until the desired response is observed or until the patient exhibits side effects. A single daily dosage may be applicable, but division of the daily dose into 2 or 3 portions is also possible. One skilled in the art is familiar with methods and techniques to optimize an effective dose and minimize toxic and adverse effects in a dose. One can rely on methods and techniques known in the art (See *Remington's Pharmaceutical Sciences*, Genero, et al. eds., 18th Edition, Easton: Mack Publishing Co.; U.S. Pat. Nos. 4,782,060, 4,771,053, 5,478,572, and 5,468,749, each specifically incorporated herein by reference).

EXAMPLE 4

Purification of Bioactive Gepirone Metabolites

As noted above, 3-OH gepirone can be prepared by chemical synthesis or enzymatic methods. Purification of 3-OH gepirone from either method can be achieved with HPLC methods using conventional techniques known in the art. The other bioactive gepirone metabolites can be prepared in similar ways.

Figure 1:
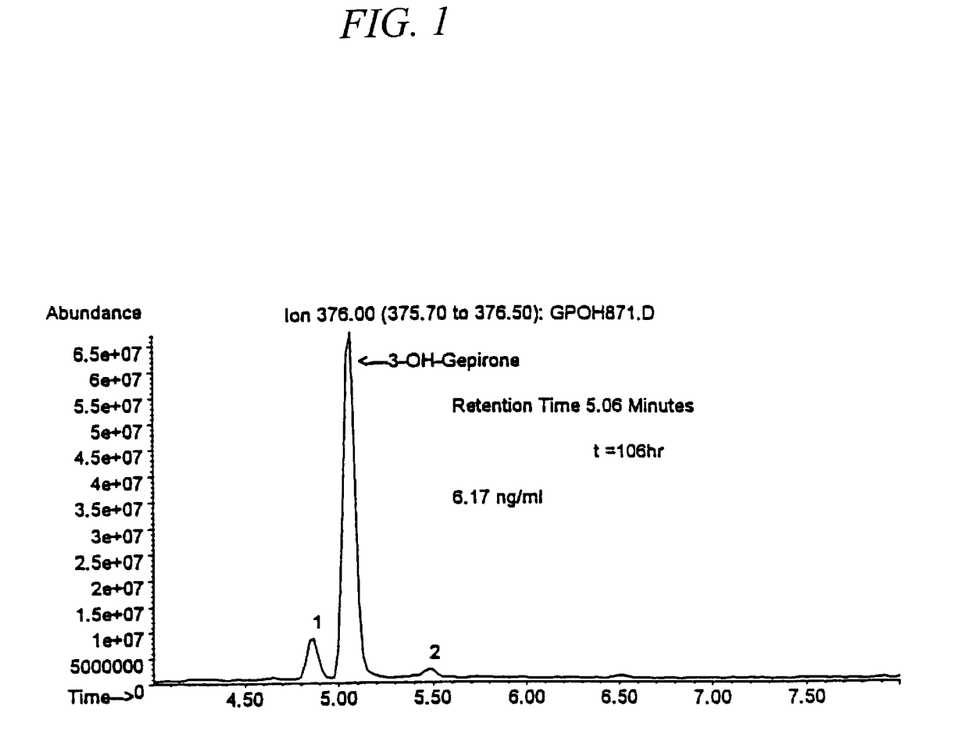
FIG. 1 depicts a chromatograph of bioactive gepirone metabolites isolated from a plasma sample: a large peak of 3-OH gepirone (labeled), 5-OH gepirone (peak 2), and 5-Me-OH gepirone (peak 1).

In FIG. 1, the purified gepirone metabolites are separated by HPLC using conditions as described below. Peaks showing 3-OH gepirone and 5-OH gepirone are identified in Figure, demonstrating the effectiveness of HPLC separation with C18 columns. The data in FIG. 1 was prepared using an electrospray-HPLC/MS analysis of a 10 ul sample from plasma. A linear gradient of 95% buffer A to 50% buffer A in 8.0 minutes was used (buffer A is aqueous 750 uM ammonium formate and mobile phase B is 80:20 acetonitrile:water (acidified with 0.15% formic acid)). A Luna 5u C18 (2) 150×1.0 mm HPLC column was used (Phenomenex).

EXAMPLE 5

Determination of 3-OH Gepirone Concentrations in Plasma

FIG. 2 shows the concentration of 3-OH gepirone in plasma of human subjects. Each sample corresponds to a 0.5 ml plasma sample, extracted with 6 ml of (2:1) (v/v) hexane:chloroform for 1 hour. After separation by centrifuge, the organic layer is transferred to a 10 ml conical tube and 90 ul of 1% formic acid is added. The tube is vortexed for 10 minutes and centrifuged for 5 minutes. About 80 ul of the formic acid layer is transferred into injection vials for HPLC/MS analysis. The electrospray-HPLC/MS system noted in Example 4 above, as described for FIG. 1, can be used to determine the levels of 3-OH gepirone.

The bioactive gepirone metabolites exemplified by formula (I), 3-OH gepirone, are useful psychotropic agents, which exhibit selective anxiolytic and antidepressant action. In particular, these improved compounds appear to offer an advantage over buspirone and its close analogs in that antipsychotic or neuroleptic action, with its potential adverse side effects, appears markedly reduced or absent. This realizes one objective of the instant invention, i.e., to increase selectively for this class of antidepressant and anxiolytic agents. Various in vivo and in vitro animal tests confirm that while the formula (I) compounds exhibit little antipsychotic activity, they otherwise retain or improve upon the novel anxioselective and anditdepressant profile exhibited by buspirone and its close analogs.

The examples and description above are exemplary and should not be taken as a limitation to the scope of the invention or the claims that follow. One skilled in the art is familiar with a variety of techniques to deduce and test variations or derivatives of the methods, compositions, and formulations described that fall within the scope of this invention. Preparing and using these variations or derivatives is enabled by this specification in the hands of those skilled in the art.

We claim:

1. A method of alleviating depression or anxiety or symptoms thereof in a mammal comprising administering an effective amount of a gepirone metabolite, or a pharmaceutically acceptable salt or hydrate thereof, to the mammal, wherein the gepirone metabolite is 3-OH gepirone or 3,5-dihydroxy gepirone.

2. The method of claim 1 wherein the gepirone metabolite is 3-OH gepirone or a pharmaceutically acceptable salt or hydrate thereof.

3. The method of claim 1, wherein the gepirone metabolite is 3,5-dihydroxy gepirone of a pharmaceutically acceptable salt or hydrate thereof.

4. The method of claim 1, wherein the amount of gepirone metabolite is about 0.1 to about 2 mg per kg of body weight.

5. The method of claim 2, wherein the amount of 3-OH gepirone is about 0.1 to about 2 mg per kg of body weight.

6. The method of claim 3, wherein the amount of 3,5-dihydroxy gepirone is about 0.1 to about 2 mg per kg of body weight.

7. The method of claim 1, wherein the bioactive gepirone metabolite is present in the plasma of the mammal at about 1 to about 5 ng/ml within two hours of administration.

8. The method of claim 2, wherein the 3-OH gepirone is present in the plasma of the mammal at about 1 to about 5 ng/ml within two hours of administration.

9. The method of claim 3, wherein the 3,5-dihydroxy gepirone is present in the plasma of the mammal at about 1 to about 5 ng/ml within two hours of administration.

10. A method for ameliorating an undesirable psychological state in a mammal comprising administering to the mammal of an effective, non-toxic dose of a bioactive gepirone metabolite, wherein the gepirone metabolite is 3-OH gepirone or 3,5-dihydroxy gepirone and wherein the undesirable psychological state is selected from the group consisting of depression, anxiety, generalized anxiety disorder, panic disorder, obsessive compulsive disorder, alcohol abuse, addiction, atypical depression, infantile autism, major depressive disorder, depression with melancholia, premenstrual syndrome, and attention deficit hyperactivity disorder.

11. The method of claim 10, wherein the gepirone metabolite is 3-OH gepirone.

12. The method of claim 10, wherein the gepirone metabolite is 3,5-dihydroxy gepirone.

13. The method of claim 11, wherein the amount of 3-OH gepirone is about 0.1 to about 2 mg per kg of body weight.

14. The method of claim 12, wherein the amount of 3,5-dihydroxy gepirone is about 0.1 to about 2 mg per kg of body weight.

15. The method of claim 11, wherein the 3-OH gepirone is present in the plasma of the mammal at about 1 to about 5 ng/ml within two hours of administration.

16. The method of claim 12, wherein the 3,5-dihydroxy gepirone is present in the plasma of the mammal at about 1 to about 5 ng/ml within two hours of administration.

17. A composition consisting essentially of 3-OH gepirone and a therapeutically acceptable carrier or excipient.

18. The composition of claim 17, formulated in an oral dosage form.

19. The composition of claim 17, formulated in an extended release form.

20. A composition consisting essentially of 3,5-dihydroxy gepirone and a therapeutically acceptable carrier or excipient.

21. The composition of claim 20, formulated in an oral dosage form.

22. The composition of claim 20, formulated in an extended release form.

23. A method of alleviating depression or symptoms thereof in a mammal comprising administering an effective amount of a gepirone metabolite, or a pharmaceutically acceptable salt or hydrate thereof, to the mammal, wherein the gepirone metabolite is 5-OH gepirone.

24. The method of claim 23, wherein the amount of 5-OH gepirone is about 0.1 to about 2 mg per kg of body weight.

25. The method of claim 23, wherein the 5-OH gepirone is present in the plasma of the mammal at about 1 to about 5 ng/ml within two hours of administration.

26. A method for ameliorating an undesirable psychological state in a mammal comprising administering to the mammal of an effective, non-toxic dose of a bioactive gepirone metabolite, wherein the gepirone metabolite is 5-OH gepirone and wherein the undesirable psychological state is selected from the group consisting of depression, generalized anxiety disorder, panic disorder, obsessive compulsive disorder, alcohol abuse, addiction, atypical depression, infantile autism, major depressive disorder, depression with melancholia, premenstrual syndrome, and attention deficit hyperactivity disorder.

27. The method of claim 26, wherein the amount of 5-OH gepirone is about 0.1 to about 2 mg per kg of body weight.

28. The method of claim 26, wherein the 5-OH gepirone is present in the plasma of the mammal at about 1 to about 5 ng/ml within two hours of administration.

29. A composition comprising 3-OH gepirone and a therapeutically acceptable carrier or excipient, wherein said composition is formulated in a dosage form selected from the group consisting of an oral dosage form, an intravenous injection form, an intramuscular injection form, a transdermal delivery form, and an extended release form.

30. The composition of claim 29, formulated in an oral dosage form.

31. The composition of claim 29, formulated in an intravenous injection form.

32. The composition of claim 29, formulated in an intramuscular injection form.

33. The composition of claim 29, formulated in a transdermal delivery form.

34. The composition of claim 29, formulated in an extended release form.

35. A composition comprising 3,5-dihydroxy gepirone and a therapeutically acceptable carrier or excipient, wherein said composition is formulated in a dosage form selected from the group consisting of an oral dosage form, an intravenous injection form, an intramuscular injection form, a transdermal delivery form, and an extended release form.

36. The composition of claim 35, formulated in an oral dosage form.

37. The composition of claim 35, formulated in an intravenous injection form.

38. The composition of claim 35, formulated in an intramuscular injection form.

39. The composition of claim 35, formulated in a transdermal delivery form.

40. The composition of claim 35, formulated in an extended release form.

* * * * *